United States Patent
Lane et al.

(10) Patent No.: US 12,281,064 B2
(45) Date of Patent: Apr. 22, 2025

(54) METHODS FOR DEHYDROGENATION OF PERHYDRO-BENZYLTOLUENE

(71) Applicant: CHEVRON U.S.A. INC., San Ramon, CA (US)

(72) Inventors: Christopher Declan Lane, San Ramon, CA (US); Steven Xuqi Song, San Ramon, CA (US); Bi-Zeng Zhan, San Ramon, CA (US); Trenton J. Otto, San Ramon, CA (US); Michael J. Girgis, San Ramon, CA (US); Yaofan Yi, San Ramon, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 18/237,157

(22) Filed: Aug. 23, 2023

(65) Prior Publication Data

US 2025/0066271 A1 Feb. 27, 2025

(51) Int. Cl.
C07C 5/367 (2006.01)
C07C 7/04 (2006.01)

(52) U.S. Cl.
CPC ............... *C07C 5/367* (2013.01); *C07C 7/04* (2013.01)

(58) Field of Classification Search
CPC .................................. C07C 7/04; C07C 5/367
See application file for complete search history.

(56) References Cited

U.S. PATENT DOCUMENTS

| | | |
|---|---|---|
| 10,260,680 B2 | 4/2019 | Arlt et al. |
| 10,396,388 B2 | 8/2019 | Bösmann et al. |
| 10,450,194 B2 | 10/2019 | Boesmann et al. |
| 2023/0137373 A1 | 5/2023 | Blanc et al. |

FOREIGN PATENT DOCUMENTS

| | | | |
|---|---|---|---|
| WO | WO-2022054013 A1 * | 3/2022 | ............ B01J 21/063 |
| WO | 20220208331 A1 | 10/2022 | |

OTHER PUBLICATIONS

International Search Report and Written Opinion dated Oct. 30, 2024 issued in PCT/US2024/43356.

* cited by examiner

*Primary Examiner* — Thuan D Dang
(74) *Attorney, Agent, or Firm* — HUNTON ANDREWS KURTH LLP (57) ABSTRACT

Methods for dehydrogenation of perhydro-benzyltoluene are described. The representative two stage reaction processes described herein provide cost-effective high amount of conversion to hydrogen and/or other beneficial products.

11 Claims, 6 Drawing Sheets

METHODS FOR DEHYDROGENATION OF PERHYDRO-BENZYLTOLUENE

FIELD OF THE DISCLOSURE

The present disclosure relates to methods for dehydrogenation of perhydro-benzyltoluene.

BACKGROUND AND SUMMARY

Storage and transportation of hydrogen is a key enabling technology for the development of a hydrogen based value-chain. Liquid organic hydrogen carriers (LOHC) are one of the various technologies currently being investigated for hydrogen transportation. The storage and transportation of hydrogen fuel from its production location to its end user site are costly with the current technology. Liquid organic hydrogen carriers are widely explored, such as dibenzyltoluene, benzyltoluene, methyl-cyclohexane, N-ethylcarbozole, ammonia borane, ammonia, formic acid, siloxane, etc. Hydrogen is chemically bonded with LOHC through hydrogenation reaction at the hydrogen production location and released through dehydrogenation reaction at the hydrogen end user site.

Important technological barriers to LOHC scale-up include: 1. Selection of appropriate carrier molecule; 2. High heat utilization efficiency; 3. Efficient dehydrogenation process at high conversion to minimize overall cost of hydrogen transportation cycle.

Many other academic and industrial R&D groups are currently exploring potential technologies for the efficient dehydrogenation of LOHC's. Although many carriers have been studied, benzyltoluene (also referred to as BT or OH-BT) is considered to have various advantages that make it a suitable candidate for scale-up as a potential LOHC carrier.

There is limited prior art that addresses heat efficiency in the process, the disclosed invention specifically claims to provide high heat integration and utilization that may approach the ideal process heat efficiency. Finally, while some other patents have focused on reactor design for the dehydrogenation process, these concepts are not yet proven at a commercially viable scale. Thus, there are deficiencies in the prior art that can be improved upon.

In some aspects, the techniques described herein relate to a method for dehydrogenation including: pre-heating perhydrobenzyl toluene (also referred to p-BT or 12H-BT) from a storage tank; co-feeding the pre-heated p-BT and hydrogen into a downflow fixed-bed reactor; raising the temperature of the p-BT and hydrogen feed mixture to approximately 500° F. or more at the entrance of the reactor; allowing a highly endothermic reaction to occur for a pre-determined time period; introducing the partially converted product from the first-stage reactor into a reflux drum in the integrated gas-phase reactor and distillation column process; quenching the second-stage reactor effluent using the partially converted product to bring the temperature below the boiling point of perhydro-benzyltoluene (also referred to as 12H-BT); separating the gas-liquid mixture in the reflux drum, removing hydrogen product (both from the first-stage and the second-stage dehydrogenation reactors) with minimal benzyltoluene (also referred to as BT) vapor, and cooling it for compression; circulating the liquid fraction from the reflux drum back into the distillation column; utilizing the heat removed by the endothermic reaction and the quenching process to maintain a temperature gradient along the length of the distillation column; and controlling the reflux ratio within the distillation column based on the total heat removal capacity of the reaction and the quenching process.

Further features of the disclosed systems and methods, and the advantages offered thereby, are explained in greater detail hereinafter with reference to specific example embodiments illustrated in the accompanying drawings.

BRIEF DESCRIPTION OF THE DRAWINGS

In order to facilitate a fuller understanding of the present invention, reference is now made to the attached drawings. The drawings should not be construed as limiting the present invention, but are intended only to illustrate different aspects and embodiments of the invention.

DETAILED DESCRIPTION

Exemplary embodiments of the invention will now be described in order to illustrate various features of the invention. The embodiments described herein are not intended to be limiting as to the scope of the invention, but rather are intended to provide examples of the components, use, and operation of the invention.

Furthermore, the described features, advantages, and characteristics of the embodiments may be combined in any suitable manner. One skilled in the relevant art will recognize that the embodiments may be practiced without one or more of the specific features or advantages of an embodiment. In other instances, additional features and advantages may be recognized in certain embodiments that may not be present in all embodiments.

The flowchart and block diagrams in the Figures illustrate the functionality and/or operation of possible implementations of systems, methods, and compositions according to various embodiments of the present invention. In this regard, each block in the flowchart or block diagrams may represent a module, segment, or portion of instructions, which comprises one or more ways for implementing the specified step. In some alternative implementations, the steps noted in the block may occur out of the order noted in the figures. For example, two blocks shown in succession may, in fact, be executed substantially concurrently, or the blocks may sometimes be executed in the reverse order, depending upon the functionality involved. A block may represent one or more vessels and also may include the addition of heat to the one or more vessels. Moreover, a block may represent a number of integrated steps. That is, the blocks simply represent steps or a combination of steps but may not necessarily represent all the equipment that may be employed.

The disclosed invention addresses deficiencies in LOHC dehydrogenation. That is, the presently disclosed methods may provide commercial scale dehydrogenation of perhydro-benzyltoluene that results in nearly complete (>90, or >95, or greater than 97% up to almost 100%) dehydrogenation of the carrier perhydro-benzyltoluene while using conventional or slightly modified reactors. Additionally, while the heat requirement for the dehydrogenation reaction is broadly considered to be a barrier for the LOHC technology, the disclosed processes provide high heat integration and/or utilization that may approach ideal process heat efficiency. Additionally, the reactors such as the second reactor may operate under conditions that are consistent with existing reactor technology eliminating costly retrofits or new designs.

In some embodiments the processes are for the dehydrogenation of perhydro-benzyltoluene (12H-BT) to products including, for example, benzyltoluene (OH-BT) and hydrogen ($H_2$). The processes utilize heat from an available heat source and may be in some embodiments mostly indifferent to the source of heat (heat transfer fluid, electrical, solar, etc.). Advantageously, waste heat which is lower value and more cost effective may be utilized as opposed to generated or produced heat. In particular, waste heat generated by processes that utilize hydrogen via either a combustion or a high temperature fuel cell process may be employed. A specific example is the utilization of waste heat from the heat recovery unit (HRU) of a turbine power generating plant, where the turbine utilizes hydrogen, at least in part, or in a mixture with, for example, natural gas, as a fuel source. The recovered heat from a power-generating turbine is sufficient in some embodiments to supply at least a portion up to all of the required heat for the disclosed processes.

Figure 1:
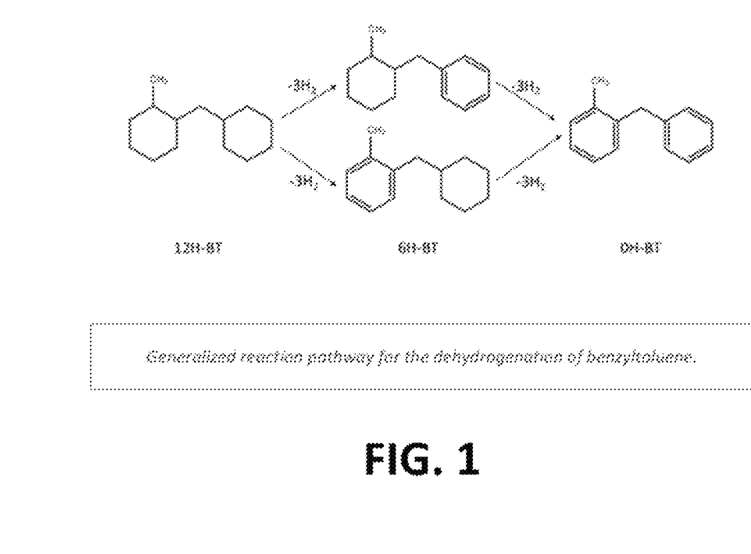
FIG. 1 illustrates a generalized reaction pathway for the dehydrogenation of perhydro-benzyltoluene according to an exemplary embodiment.

The generalized reaction pathway for the dehydrogenation process is illustrated in FIG. 1. For simplicity only the meta isomer (1-benzyl-2-methylbenzene) is shown, however it is understood that benzyltoluene may have an isomer composition of, for example, 50% para (1-benzyl-4-methylbenzene), 45% meta isomer ((1-benzyl-4-methylbenzene), and 5% ortho isomer (1-benzyl-3-methylbenzene).

Figure 2:
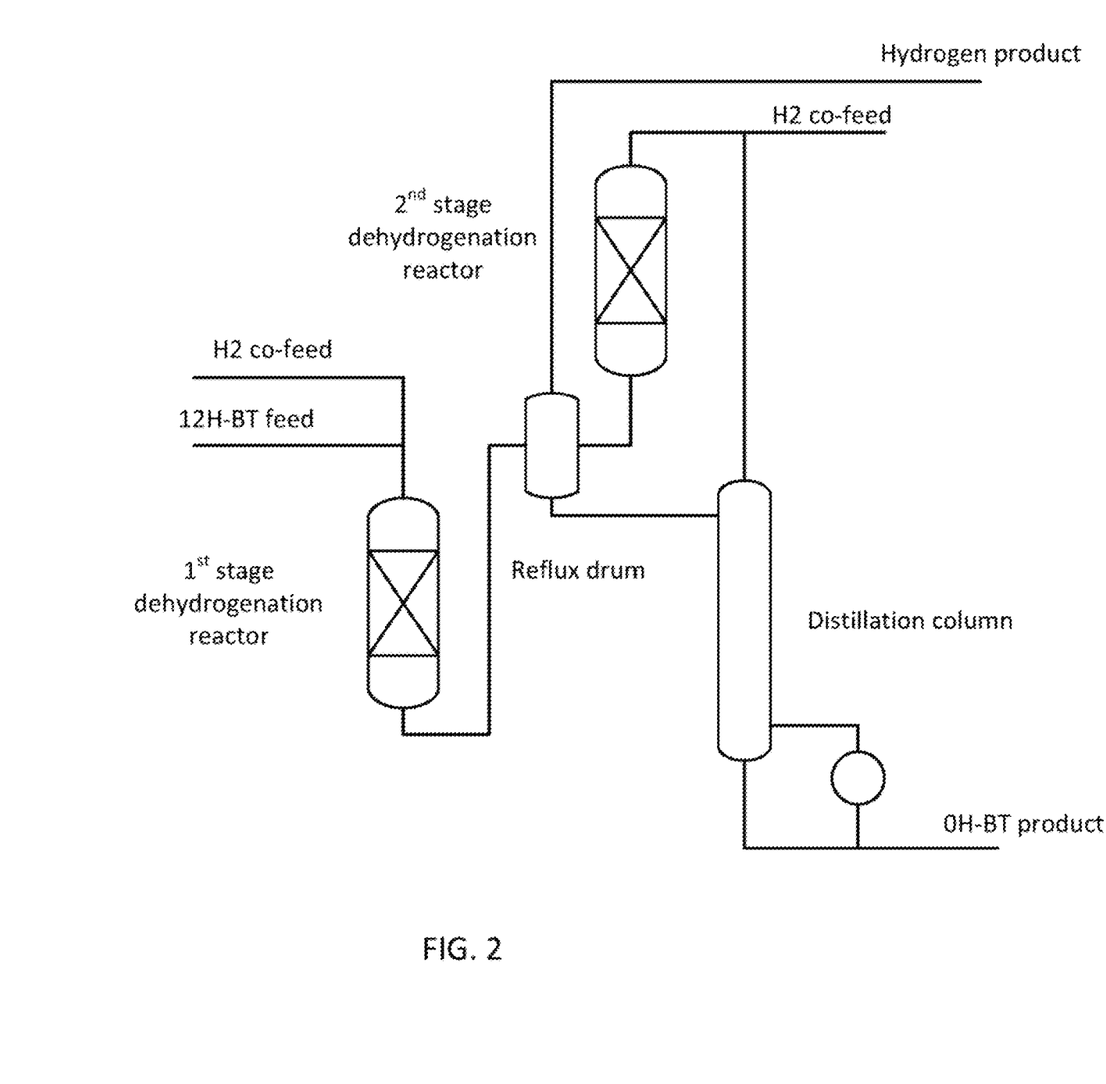
FIG. 2 is a flow diagram illustrating a process according to an exemplary embodiment.

The processes are further illustrated, in-part, by FIG. 2. The process may be conceptually divided into a first-stage dehydrogenation process and a second-stage dehydrogenation process, which, as described above, together are capable of achieving >97% or more degree of dehydrogenation of the perhydro-benzyltoluene feedstock (12H-BT). For clarity each stage is described separately.

First-Stage Dehydrogenation

First-stage dehydrogenation may be conducted in a downflow fixed-bed reactor. Fresh p-BT from a storage tank is pre-heated and co-fed into the reaction vessel with hydrogen. The ratio of $H_2$:p-BT can be approximately 6000 scf/bbl and may be lower (in a range of 0 to 8000 scf/bbl, preferably from about 700, or from about 1000 to about 6000 scf/bbl), the addition of hydrogen to the feed provides sufficient hydrogen-partial pressure to assist in diminishing and/or minimizing the formation of coke within the reactor and particularly on the catalyst. Since the reaction produces hydrogen as a product, the co-feed of hydrogen may assist to minimize the coke formation at the top of the first catalyst bed before sufficient hydrogen has been produced to mitigate coke formation.

The temperature of the feed mixture comprising p-BT and hydrogen is raised to approximately 500° F. at the entrance to the reactor. The reaction is highly endothermic and the outlet temperature of the reactor is estimated to be approximately from about 420° F. to about 600° F., or about 500° F. Additional heat can be supplied from various heat sources through the heat transfer surface in the catalyst bed. For these conditions it is expected that the 12H-BT feed stock will be partially converted in a first stage resulting in a degree of dehydrogenation of approximately 15%-50% with a target between 30%-35%. The estimate of partial conversion is based on experimental data as illustrated in Tables 1 and 2 below. The first-stage reactor operated at a lower temperature than the second-stage. The lower operating temperature allows for unutilized heat from the second-stage to be used as a heat source for the first-stage reactor. By operating the first-stage at lower temperature, there is a significant benefit to the processes overall utilization of energy from the heat source. Additionally, the first-stage reactor is more cost-efficient equipment per degree of conversion and is less complex than the equipment used in the second-stage. Therefore, overall plant costs (CAPEX and OPEX) are reduced by minimizing the capacity and therefore equipment sizes in the second-stage by partially dehydrogenating p-BT with cost-effective equipment in the first-stage. Further, one may achieve the additional operational benefits from employing a fixed-bed reactor.

Figure 3:
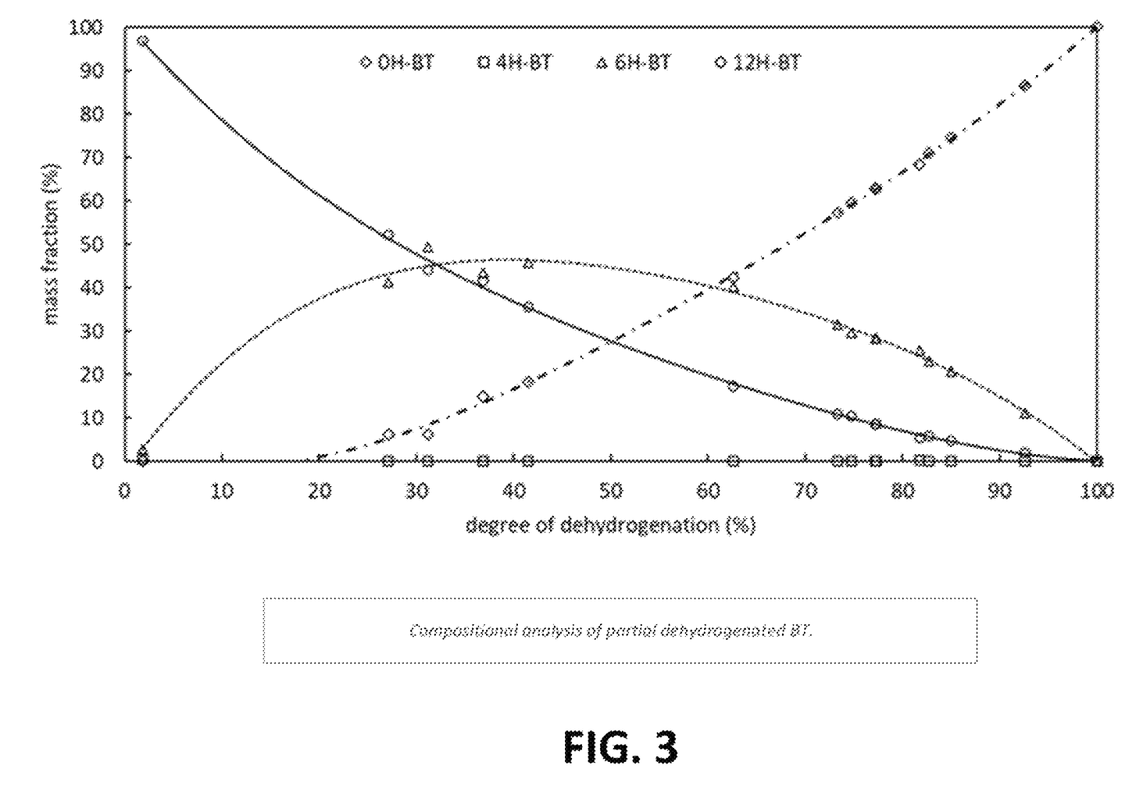
FIG. 3 illustrates a compositional analysis of partially converted mixtures in a bench scale research unit experiment.

The first-stage reactor partially converts the 12H-BT to a mixture of 12H-BT, 6H-BT, and OH-BT. Compositional analysis of partially converted mixtures are presented in FIG. 3. It is therefore expected that the first-stage reaction results in a partially dehydrogenated BT mixture with an approximate composition of 35-45% 12H-BT, 45% 6H-BT, 10-20% OH-BT plus hydrogen product. Based on adiabatic reactor conditions, and assuming negligible process heat losses, the heat supply required for the reaction is approximately +65.4±1.1 kJ mol$^{-1}$ ($H_2$) at standard conditions or about +70.2±1.1 kJ mol$^{-1}$ ($H_2$) at 300° C., respectively. The reactor effluent is a gas-liquid mixture and is separated by phase immediately after the reaction vessel. Hydrogen product may be combined with hydrogen produced from the second-stage reaction and liquid product may be combined with the products form the second-stage reactor.

Second-Stage Dehydrogenation:

The second-stage of the dehydrogenation process may result in a degree of dehydrogenation of greater than about 90%, or greater than about 95%, or greater than about 97.1% or even more up to almost 100%, by utilizing an integrated reaction-distillation process. Unlike prior reaction-distillation processes the instant processes separate the reaction and distillation into separated process vessels. This advantageously allows for the reaction to occur solely or near solely in the gas phase which is very different from prior art multiphase reaction-distillation setups. In particular, the prior art multiphase reaction-distillation processes may have various technical challenges that are prohibitive at commercial scale. These challenges include, for example, catalyst form factor and that the dehydrogenation process required long residence times in the presence of a catalyst. However, to allow for the distillation process to occur, there must be sufficient voidage in the catalyst bed to allow for counter-current gas-liquid flow. Without sufficient bed voidage, the counter-current flow regime may not be maintained leading to flooding in the packed bed. This problem is exacerbated in the prior art processes because they require longer columns as the total gas and liquid fluxes increase proportional to the length of the catalyst bed. The catalyst in the prior art processes also has low active metal loading in comparison to a typical packed bed with extrudate catalyst. Thus, the present processes may avoid one or more up to all of the aforementioned disadvantages.

The second-stage reaction process is an integrated gas-phase reactor and distillation column. Partially converted product from the first-stage reactor is introduced into the reflux drum. The partially converted product is usually at a lower temperature than the second-stage reactor product and thus advantageously may be used to quench the second-stage reactor gas-stream. The quench is useful prior to the reflux to ensure the stream is below the 12H-BT boiling point. The reflux drum separates the gas-liquid mixture, removing hydrogen product (often with reduced or minimal BT vapor) which is combined with hydrogen product from the first-stage dehydrogenation and subsequently cooled to a temperature suitable for gas-compression. The hydrogen cooling process may also remove at least some up to all BT condensate that can be recycled back into the process, though depending upon conditions this could be a relatively small mass flow due to the low BT vapor pressure after cooling.

Liquid from the reflux drum is circulated back to the distillation column. At least a portion up to all of the heat removed by the endothermic reaction and the quench is sufficient to maintain the temperature gradient along at least a portion up to all of the length of the distillation column. More specifically the reflux ratio may in some cases be limited by the total heat removal capacity of the reaction and the quench.

Figure 4:
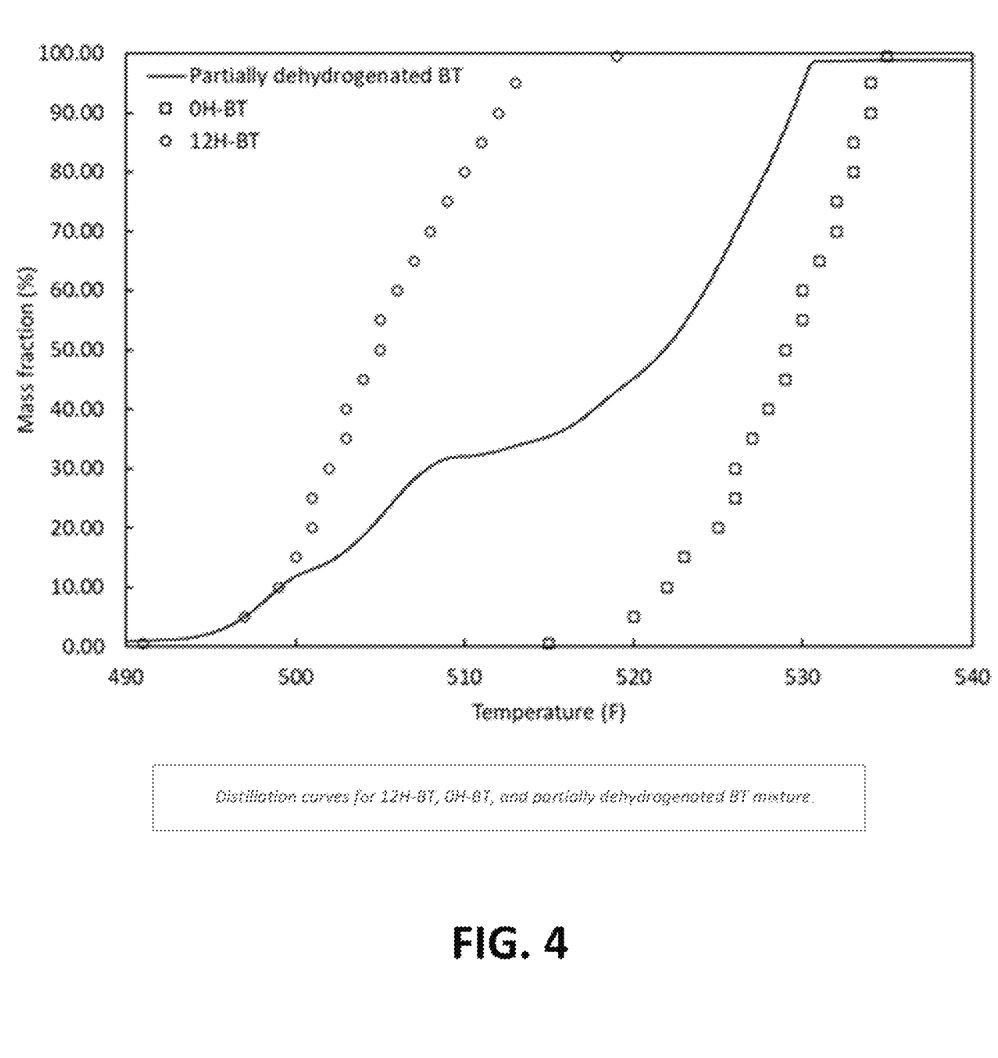
FIG. 4 illustrates experimental distillation curves.
Figure 5:
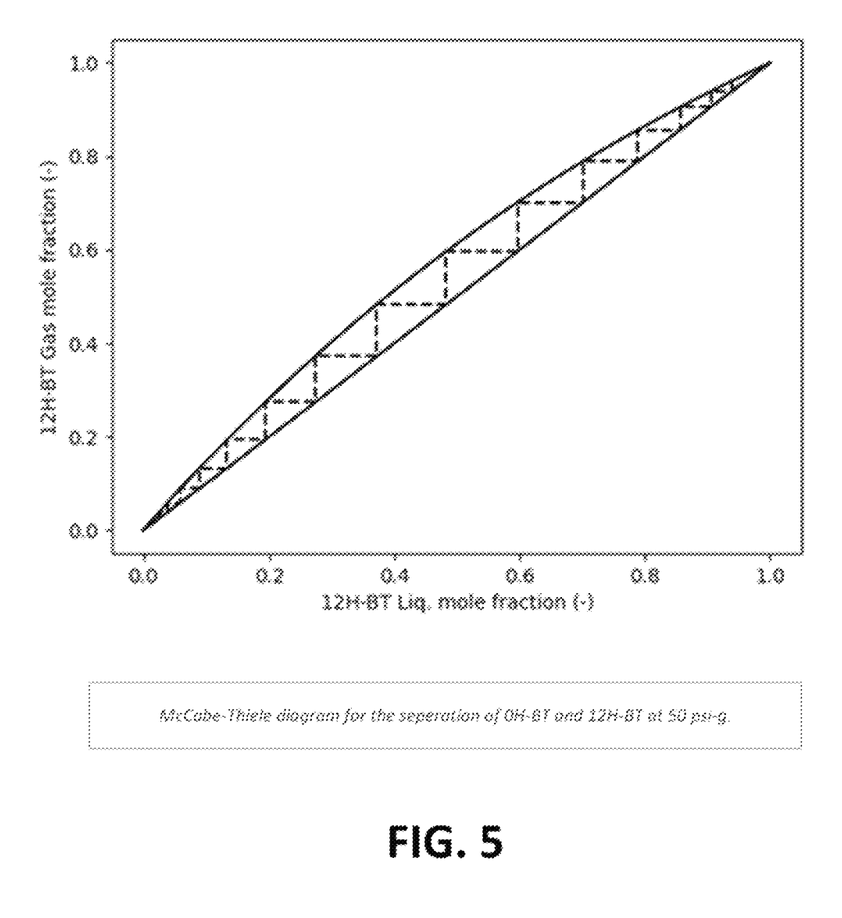
FIG. 5 illustrates a McCabe-Thiele diagram for the separation of benzyltoluene and perhydrobenzyltoluene at 50 psi-g.
Figure 6:
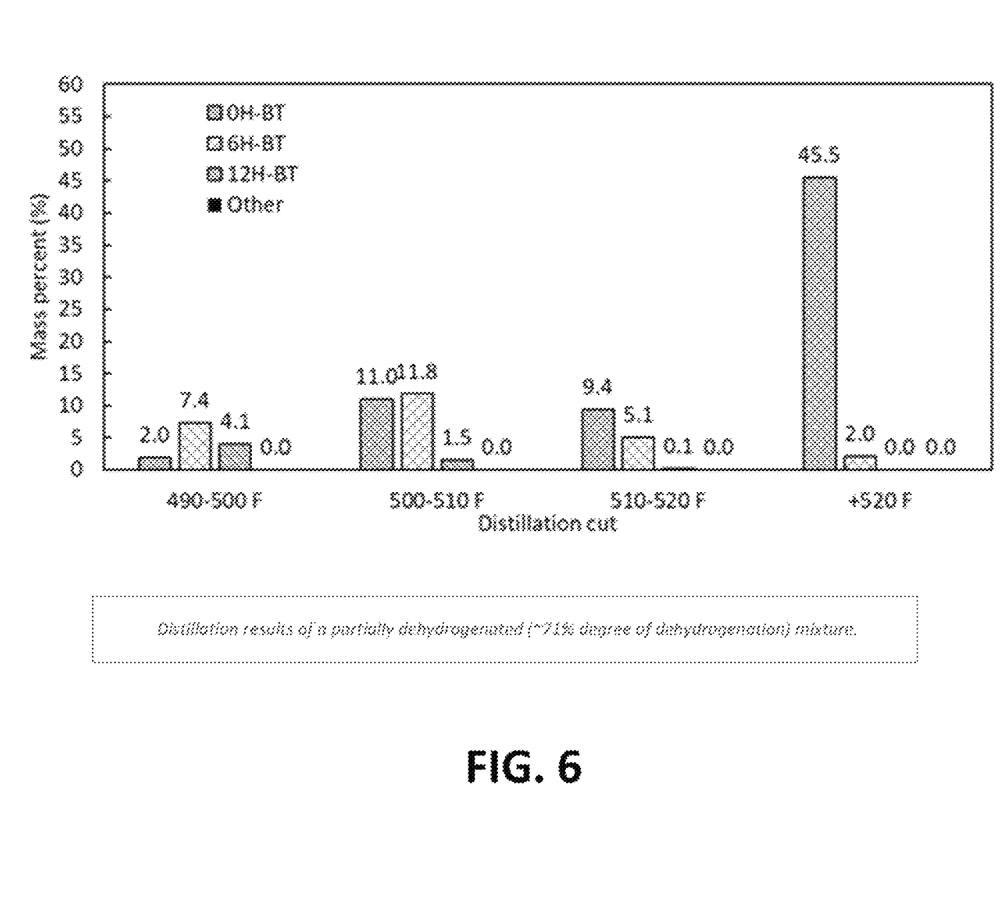
FIG. 6 illustrates the distillation results of a partially dehydrogenated (~71% degree of dehydrogenation) mixture.

The column may operate as a typical distillation column and also may utilize either trays, packing, or a combination to enhance gas-liquid contact and/or mass transfer. From experimental distillation curves (FIG. 4), it is expected that approximately 20 theoretical plate equivalents along the column length could be employed in some embodiments for the effective separation of OH-BT from 6H-BT and 12H-BT (FIG. 5). The distillation column uses a reboiler arrangement that may be conventional or varied depending upon the application. The bottoms may comprise a BT mixture with at least about 90, or at least about 95, or at least about 97.1% or more as OH-BT which may be sent out as lean LOHC in the next cycle of hydrogen transport (FIG. 6). Heat may be supplied to the reboiler from a heat source as previously described and is alternatively or additionally potentially supplied by steam from a heat recovery unit for a process which utilizes hydrogen as a fuel source.

The present processes may advantageously utilize the reboiler heat source for the second-stage reaction which may then be subsequently used as a heat source for the first-stage reaction. The use of the reboiler waste-heat for the first-stage reactor may materially improve the overall utilization of the heat source, in the case of a heat transfer fluid being used to supply process heat.

The distillation tower tops are fed to the second-stage reactor which often operates in the gas-phase with heterogenous catalyst. The catalyst is typically a noble metal (group VIII) catalyst such as Pt on $Al_2O_3$. The reactor inlet may be from about 520° F. up to about 700° F., or approximately 600° F. and the BT may be mixed with a stream of hydrogen prior to contacting the catalyst bed. The hydrogen co-feed advantageously may reduce the rate of catalyst deactivation by maintaining $H_2$ partial pressure near the entrance of the catalyst bed and also may act as a stripping gas to prevent condensation of BT, particularly OH-BT. The mass flow rate through the reactor in some case could be related or limited by the reflux ratio as previously described. The reactor in some embodiment partially converts the gas mixture which is expected to be a mixture of 6H-BT and 12H-BT to a mixture of OH-BT, 6H-BT, and 12H-BT. The overall degree of dehydrogenation of the mixture is improved over prior art processes.

In some aspects, the techniques described herein relate to a method for dehydrogenation including: pre-heating p-BT from a storage tank; co-feeding the pre-heated p-BT and hydrogen into the downflow fixed-bed reactor; raising the temperature of the mixture comprising the p-BT:hydrogen feed to at least about approximately 500° F. at the entrance of the reactor; allowing the highly endothermic reaction to occur for a predetermined time period, introducing the partially converted product from the first-stage reactor into a reflux drum in the integrated gas-phase reactor and distillation column process; quenching the second-stage reactor gas-stream using at least a portion of the partially converted product to bring the temperature below the boiling point of 12H-BT; separating the gas-liquid mixture in the reflux drum, removing hydrogen product with minimal BT vapor, combining it with the hydrogen product obtained from the first-stage dehydrogenation, and cooling it for compression; recycling BT condensate, resulting from the cooling process, back into the process; circulating the liquid fraction from the reflux drum back into the distillation column; utilizing the heat removed by the endothermic reaction and the quenching process to maintain a temperature gradient along the length of the distillation column; controlling the reflux ratio within the distillation column based on the total heat removal capacity of the reaction and the quenching process.

In some aspects, the techniques described herein relate to a method, wherein maintaining a $H_2$:p-BT ratio in the range of from about 0 to about 8000 scf/bbl, wherein the ratio may be approximately 6000 scf/bbl.

In some aspects, the techniques described herein relate to a method, wherein the outlet temperature of the reactor estimated to be approximately 460° F.

In some aspects, the techniques described herein relate to a method, wherein the method further includes providing a sufficient hydrogen-partial pressure in the reactor to minimize coke formation on the catalyst.

Table 1 below is a table illustrating estimates of partial conversion of p-BT in the presence of catalyst A according to an exemplary embodiment.

TABLE 1

Results from catalyst A

| Temp. (F.) | Pressure (psi-g) | Liq. Hourly Space Velocity (h-1) | H2 feed rate (scf/bbl) | Time-on-stream start (h) | Time-on-stream end (h) | H wt. % | Conversion (%) |
|---|---|---|---|---|---|---|---|
| 450 | 50 | 0.10 | 6000 | 98.0 | 170.5 | 11.83 | 30.12 |
| 450 | 50 | 0.10 | 6000 | 170.5 | 194.5 | 11.92 | 28.50 |
| 450 | 50 | 0.10 | 6000 | 194.5 | 242.2 | 11.93 | 28.32 |
| 450 | 50 | 0.10 | 6000 | 242.2 | 266.2 | 12 | 27.07 |
| 450 | 50 | 0.10 | 6000 | 266.2 | 341.8 | 12.05 | 26.17 |
| 500 | 50 | 0.10 | 6000 | 411.5 | 437.5 | 11.25 | 40.42 |
| 500 | 50 | 0.10 | 6000 | 437.5 | 506.5 | 11.27 | 40.07 |
| 500 | 50 | 0.10 | 6000 | 530.5 | 677.2 | 11.42 | 37.41 |
| 500 | 50 | 0.10 | 6000 | 677.2 | 722.2 | 11.46 | 36.71 |
| 500 | 50 | 0.10 | 6000 | 722.2 | 770.2 | 11.49 | 36.17 |
| 500 | 50 | 0.10 | 6000 | 770.2 | 842.2 | 11.51 | 35.82 |
| 550 | 50 | 0.10 | 6000 | 1010.7 | 1058.7 | 10.07 | 60.98 |
| 550 | 50 | 0.10 | 6000 | 1058.7 | 1106.2 | 10.2 | 58.74 |
| 550 | 50 | 0.10 | 6000 | 1106.2 | 1178.5 | 10.3 | 57.01 |
| 550 | 50 | 0.10 | 6000 | 1178.5 | 1226.0 | 10.41 | 55.11 |
| 550 | 50 | 0.10 | 6000 | 1730.8 | 1778.0 | 11.31 | 39.36 |
| 600 | 50 | 0.10 | 6000 | 1853.0 | 1928.0 | 8.74 | 83.51 |
| 600 | 50 | 0.10 | 6000 | 1928.0 | 2022.0 | 8.8 | 82.51 |
| 600 | 50 | 0.10 | 6000 | 2022.0 | 2067.5 | 8.83 | 82.01 |
| 600 | 50 | 0.10 | 6000 | 2067.5 | 2114.2 | 8.86 | 81.50 |
| 600 | 50 | 0.10 | 6000 | 2114.2 | 2192.8 | 8.93 | 80.33 |
| 600 | 50 | 0.10 | 6000 | 2192.8 | 2258.5 | 8.98 | 79.49 |
| 600 | 50 | 0.10 | 6000 | 2258.5 | 2282.0 | 9.04 | 78.48 |
| 600 | 50 | 0.10 | 6000 | 2428.7 | 2453.3 | 9.41 | 72.24 |

TABLE 1-continued

Results from catalyst A

| Temp. (F.) | Pressure (psi-g) | Liq. Hourly Space Velocity (h-1) | H2 feed rate (scf/bbl) | Time-on-stream start (h) | Time-on-stream end (h) | H wt. % | Conversion (%) |
|---|---|---|---|---|---|---|---|
| 600 | 50 | 0.10 | 6000 | 2428.7 | 2453.3 | 9.41 | 72.24 |
| 600 | 50 | 0.10 | 6000 | 2453.3 | 2525.2 | 9.26 | 74.78 |
| 600 | 50 | 0.10 | 6000 | 2525.2 | 2573.2 | 9.22 | 75.45 |
| 600 | 50 | 0.10 | 6000 | 2573.2 | 2597.1 | 9.39 | 72.58 |
| 650 | 50 | 0.10 | 6000 | 2745.5 | 2765.5 | 8.32 | 90.49 |
| 650 | 50 | 0.10 | 6000 | 2765.5 | 2789.1 | 8.29 | 90.98 |
| 650 | 50 | 0.10 | 6000 | 2789.1 | 2861.6 | 8.41 | 89.00 |
| 650 | 50 | 0.10 | 6000 | 2861.6 | 2885.2 | 8.52 | 87.17 |
| 650 | 50 | 0.10 | 6000 | 2885.2 | 2909.5 | 8.54 | 86.84 |
| 650 | 50 | 0.10 | 6000 | 2935.0 | 2957.7 | 8.74 | 83.51 |
| 650 | 50 | 0.10 | 6000 | 2944.0 | 3029.2 | 8.87 | 81.34 |
| 650 | 50 | 0.10 | 6000 | 3029.2 | 3077.1 | 9.01 | 78.99 |

Table 2 below is a table illustrating estimates of partial conversion of p-BT in the presence of catalyst B according to an exemplary embodiment.

TABLE 2

Results from catalyst B

| Temp. (F.) | Pressure (psi-g) | Liq. Hourly Space Velocity (h-1) | H2 feed rate (scf/bbl) | Time-on-stream start (h) | Time-on-stream end (h) | H wt. % | Conversion (%) |
|---|---|---|---|---|---|---|---|
| 550 | 50 | 0.10 | 6000 | 269.6 | 293.4 | 0.1197 | 27.61 |
| 550 | 50 | 0.10 | 6000 | 293.4 | 318.3 | 0.1205 | 26.17 |
| 550 | 50 | 0.10 | 6000 | 318.3 | 341.3 | 0.119 | 28.86 |
| 550 | 50 | 0.10 | 6000 | 341.3 | 414.5 | 0.1192 | 28.50 |
| 550 | 50 | 0.10 | 6000 | 414.5 | 437.3 | 0.1192 | 28.50 |
| 550 | 50 | 0.10 | 6000 | 437.3 | 461.4 | 0.1192 | 28.50 |
| 550 | 50 | 0.10 | 6000 | 461.4 | 484.0 | 0.1187 | 29.40 |
| 550 | 50 | 0.10 | 6000 | 510.5 | 581.3 | 0.1198 | 27.43 |
| 550 | 50 | 0.10 | 6000 | 581.3 | 606.0 | 0.1194 | 28.15 |
| 550 | 50 | 0.10 | 6000 | 606.0 | 628.7 | 0.1199 | 27.25 |
| 550 | 50 | 0.10 | 6000 | 628.7 | 652.7 | 0.1195 | 27.97 |
| 550 | 50 | 0.10 | 6000 | 652.7 | 677.8 | 0.1198 | 27.43 |
| 550 | 50 | 0.10 | 6000 | 677.8 | 749.8 | 0.1197 | 27.61 |
| 550 | 50 | 0.10 | 6000 | 749.8 | 773.9 | 0.1198 | 27.43 |
| 550 | 50 | 0.10 | 6000 | 773.9 | 794.0 | 0.1197 | 27.61 |
| 550 | 50 | 0.10 | 6000 | 989.6 | 1013.0 | 0.12 | 27.07 |
| 550 | 50 | 0.10 | 6000 | 1013.0 | 1085.7 | 0.1201 | 26.89 |
| 600 | 50 | 0.10 | 6000 | 1120.0 | 1156.7 | 0.0984 | 64.92 |
| 600 | 50 | 0.10 | 6000 | 1156.7 | 1180.5 | 0.0983 | 65.09 |
| 600 | 50 | 0.10 | 6000 | 1180.5 | 1248.6 | 0.0985 | 64.75 |
| 600 | 50 | 0.10 | 6000 | 1277.1 | 1301.5 | 0.0988 | 64.24 |
| 600 | 50 | 0.10 | 6000 | 1301.5 | 1326.1 | 0.0992 | 63.55 |
| 600 | 50 | 0.10 | 6000 | 1326.1 | 1349.5 | 0.0992 | 63.55 |
| 600 | 50 | 0.10 | 6000 | 1349.5 | 1420.0 | 0.0995 | 63.04 |
| 600 | 50 | 0.10 | 6000 | 1420.0 | 1445.8 | 0.0996 | 62.87 |
| 600 | 50 | 0.10 | 6000 | 1445.8 | 1470.2 | 0.0998 | 62.52 |
| 600 | 50 | 0.10 | 6000 | 1470.2 | 1494.8 | 0.0999 | 62.35 |
| 600 | 50 | 0.10 | 6000 | 1514.2 | 1614.2 | 0.1 | 62.18 |
| 600 | 50 | 0.10 | 6000 | 1614.2 | 1639.7 | 0.1002 | 61.84 |
| 600 | 50 | 0.10 | 6000 | 1639.7 | 1661.2 | 0.1002 | 61.84 |
| 650 | 50 | 0.10 | 6000 | 1758.7 | 1780.7 | 0.0843 | 88.67 |
| 650 | 50 | 0.10 | 6000 | 1780.7 | 1805.0 | 0.0845 | 88.34 |
| 650 | 50 | 0.10 | 6000 | 1805.0 | 1801.3 | 0.0846 | 88.17 |
| 650 | 50 | 0.10 | 6000 | 1801.3 | 1885.7 | 0.0847 | 88.00 |
| 650 | 50 | 0.10 | 6000 | 1885.7 | 1827.2 | 0.0849 | 87.67 |
| 650 | 50 | 0.10 | 6000 | 1827.2 | 1946.4 | 0.0849 | 87.67 |
| 650 | 50 | 0.10 | 6000 | 1946.4 | 1973.0 | 0.085 | 87.51 |
| 650 | 50 | 0.10 | 6000 | 1973.0 | 1998.6 | 0.0852 | 87.17 |
| 650 | 50 | 0.10 | 6000 | 1998.6 | 2017.8 | 0.0851 | 87.34 |
| 650 | 50 | 0.10 | 6000 | 2017.8 | 2091.8 | 0.0853 | 87.01 |
| 650 | 50 | 0.10 | 6000 | 2091.8 | 2118.4 | 0.0852 | 87.17 |
| 650 | 50 | 0.10 | 6000 | 2118.4 | 2138.3 | 0.0854 | 86.84 |
| 650 | 50 | 0.10 | 6000 | 2138.3 | 2160.9 | 0.0854 | 86.84 |

TABLE 2-continued

Results from catalyst B

| Temp. (F.) | Pressure (psi-g) | Liq. Hourly Space Velocity (h-1) | H2 feed rate (scf/bbl) | Time-on-stream start (h) | Time-on-stream end (h) | H wt. % | Conversion (%) |
|---|---|---|---|---|---|---|---|
| 650 | 50 | 0.10 | 6000 | 2185.2 | 2256.7 | 0.0855 | 86.67 |
| 650 | 50 | 0.10 | 6000 | 2256.7 | 2281.0 | 0.0854 | 86.84 |
| 650 | 50 | 0.10 | 6000 | 2256.7 | 2281.0 | 0.0854 | 86.84 |
| 650 | 50 | 0.10 | 6000 | 2281.0 | 2303.3 | 0.0851 | 87.34 |
| 650 | 50 | 0.10 | 6000 | 2303.3 | 2332.4 | 0.0845 | 88.34 |
| 650 | 50 | 0.10 | 6000 | 2332.4 | 2353.7 | 0.0845 | 88.34 |
| 650 | 50 | 0.10 | 6000 | 2353.7 | 2426.3 | 0.0846 | 88.17 |
| 650 | 50 | 0.10 | 6000 | 2426.3 | 2476.7 | 0.0848 | 87.84 |
| 650 | 50 | 0.10 | 6000 | 2476.7 | 2488.0 | 0.0849 | 87.67 |
| 650 | 50 | 0.10 | 6000 | 2512.0 | 2596.4 | 0.0850 | 87.51 |

Although embodiments of the present invention have been described herein in the context of a particular implementation in a particular environment for a particular purpose, those skilled in the art will recognize that its usefulness is not limited thereto and that the embodiments of the present invention can be beneficially implemented in other related environments for similar purposes. The invention should therefore not be limited by the above described embodiments, method, and examples, but by all embodiments within the scope and spirit of the invention as claimed.

Further, it is to be understood that the terminology used herein is for the purpose of describing particular embodiments only and is not intended to be limiting. The terms "a" or "an" as used herein, are defined as one or more than one. The term "plurality" as used herein, is defined as two or more than two. The term "another" as used herein, is defined as at least a second or more. The terms "including" and/or "having," as used herein, are defined as comprising (i.e., open language). The term "providing" is defined herein in its broadest sense, e.g., bringing/coming into physical existence, making available, and/or supplying to someone or something, in whole or in multiple parts at once or over a period of time.

In the invention, various embodiments have been described with references to the accompanying drawings. It may, however, be evident that various modifications and changes may be made thereto, and additional embodiments may be implemented, without departing from the broader scope of the invention as set forth in the claims that follow. The invention and drawings are accordingly to be regarded in an illustrative rather than restrictive sense.

The invention is not to be limited in terms of the particular embodiments described herein, which are intended as illustrations of various aspects. Many modifications and variations can be made without departing from its spirit and scope. Functionally equivalent systems, processes and apparatuses within the scope of the invention, in addition to those enumerated herein, may be apparent from the representative descriptions herein. Such modifications and variations are intended to fall within the scope of the appended claims. The invention is to be limited only by the terms of the appended claims, along with the full scope of equivalents to which such representative claims are entitled.

The preceding description of exemplary embodiments provides non-limiting representative examples referencing numerals to particularly describe features and teachings of different aspects of the invention. The embodiments described should be recognized as capable of implementation separately, or in combination, with other embodiments from the description of the embodiments. A person of ordinary skill in the art reviewing the description of embodiments should be able to learn and understand the different described aspects of the invention. The description of embodiments should facilitate understanding of the invention to such an extent that other implementations, not specifically covered but within the knowledge of a person of skill in the art having read the description of embodiments, would be understood to be consistent with an application of the invention.

What is claimed is:

1. A method for dehydrogenation comprising:
pre-heating perhydro benzyl-toluene (12H-BT);
co-feeding the pre-heated perhydro benzyl-toluene (12H-BT) with a gas comprising hydrogen into a fixed-bed reactor in a first-stage reactor wherein under conditions sufficient to produce at least a partially converted product mixture comprising 12H-BT, 6H-BT, 0H-BT, and hydrogen, wherein the amount of co-fed hydrogen is sufficient to reduce coke formation;
introducing at least a portion of the partially converted product mixture from the first-stage reactor into a second stage reactor comprising a gas-phase reactor and a distillation column at a temperature below the boiling point of 12H-BT and under gas-phase reactor conditions sufficient to produce a gas-liquid mixture comprising (1) a gas comprising hydrogen and (2) a liquid mixture comprising 12H-BT, 6H-BT, and 0H-BT;
removing a product comprising hydrogen product from second stage reactor and cooling the hydrogen product for compression; and
distilling the liquid in the distillation column to substantially separate 12H-BT, 6H-BT, and 0H-BT.

2. The method of claim 1 which further comprises recycling at least a portion of the liquid mixture comprising 12H-BT, 6H-BT, and 0H-BT to the gas phase reactor.

3. The method of claim 1 which further comprises maintaining a temperature gradient along the length of the distillation column.

4. The method of claim 1 which further comprises controlling a reflux ratio within the distillation column, wherein the reflux ratio is based on a heat removal capacity, a quenching of the reaction, or a combination thereof.

5. The method of claim 1 wherein the ratio of hydrogen to 12H-BT in the co-feed is from about 0 to about 8000 scf/bbl.

6. The method of claim 1 wherein the ratio of hydrogen to 12H-BT in the co-feed is from about 5500 scf/bbl to about 6500 scf/bbl.

7. The method of claim 1 wherein the partially converted product mixture comprising 12H-BT, 6H-BT, 0H-BT, and hydrogen exits the first stage reactor at a temperature of from about 420° F. to about 500° F.

8. The method of claim 1 wherein the degree of dehydrogenation is from about 15% to about 50% in the first stage.

9. The method of claim 1 wherein the fixed-bed reactor is a downflow fixed bed reactor.

10. The method of claim 1 wherein the perhydro benzyl-toluene (12H-BT) to be pre-heated is stored in a storage tank.

11. The method of claim 1 wherein the temperature of the co-feed is raised to from about 420° F. to about 600° F. to produce the at least partially converted product in the first stage.

* * * * *